United States Patent [19]

Imamura

[11] Patent Number: 5,013,570

[45] Date of Patent: May 7, 1991

[54] METHOD OF PRODUCING ODORLESS RIPE JUICE OF HOUTTUYNIA CORDATA

[75] Inventor: Eiyu Imamura, Higashi Yamanashi County, Japan

[73] Assignee: Yamanashi Yagen Limited, Yamanashi Prefecture, Japan

[21] Appl. No.: 523,412

[22] Filed: May 15, 1990

[30] Foreign Application Priority Data

May 16, 1989 [JP] Japan ................................ 1-120543

[51] Int. Cl.$^5$ .............................................. A23L 1/068
[52] U.S. Cl. .................................... 426/599; 426/590
[58] Field of Search .............................. 426/590, 599; 424/195.1

[56] References Cited

FOREIGN PATENT DOCUMENTS

| | | |
|---|---|---|
| 54-78672 | 4/1981 | Japan . |
| 55-1095 | 10/1981 | Japan . |
| 55-181730 | 10/1982 | Japan . |
| 56-97861 | 3/1983 | Japan . |
| 56-152318 | 6/1983 | Japan . |
| 58-134436 | 8/1985 | Japan . |
| 58-240760 | 11/1985 | Japan . |
| 59-7317 | 12/1985 | Japan . |
| 59-161115 | 7/1986 | Japan . |
| 60-89800 | 3/1987 | Japan . |
| 60-154995 | 10/1987 | Japan . |
| 62-23462 | 12/1988 | Japan . |
| 62-224817 | 6/1989 | Japan . |
| 62-177092 | 7/1989 | Japan . |

*Primary Examiner*—Carolyn Paden
*Attorney, Agent, or Firm*—Oblon, Spivak, McClelland, Maier & Neustadt

[57] ABSTRACT

A method of producing an odorless ripe dokudamiso juice comprises the steps of preparing a green juice from fresh dokudamiso, heating the green juice prepared at a temperature of 70° to 80° C. for 10 to 30 minutes or roughly filtering the prepared green juice, and oxidizing it. This method permits the dokudamiso components having medicinal effects to be easily provided at any time in a form which allows internal use.

3 Claims, No Drawings

METHOD OF PRODUCING ODORLESS RIPE JUICE OF HOUTTUYNIA CORDATA

BACKGROUND OF THE INVENTION

The present invention relates to a method of producing an odorless ripe juice containing the components of *Houttuynia cordata* (referred to as "dokudamiso" hereinafter), which have medicinal effects, from raw dokudamiso.

Dokudamiso contains abundant amounts of quercitrin, which is a flavonol glucoside having a cardiotonic function, an intestine regulating function, a blood pressure regulating function and a detoxicating function, and other components having medicinal effects. Dokudamiso has been therefore used as a folk medicine for a long time. As is generally known, however, dokudamiso has a strong, unpleasantly peculiar odor. To use it, it is therefore necessary to extract the quercitrin from dokudamiso by squeezing or leaching and then to decompose or remove the odor components.

It is known that the odor components of dokudamiso are laurin aldehyde and caprin aldehyde, which are irrelevant to the medicinal effects thereof and which can be substantially completely removed by drying or steam distillation. In most cases, dokudamiso is therefore utilized through the internal use of an odorless exudate obtained by a method of decocting dry dokudamiso. Although this method has an advantage in that the effective components of dokudamiso can be used throughout all seasons if dry dokudamiso only is prepared, it is tedious to decoct dry dokudamiso for each internal use of the odorless exudate.

A method of utilizing dokudamiso without drying is proposed in which a dokudamiso green juice is deodorized and then internally used (Japanese Patent Publication No. 59-7692). In the deodorizing method, a yeast and a carbon source therefor are inoculated into the dokudamiso green juice, which is then fermented, and the thus-obtained suspension is filtered. In this method, however, since the odor components of dokudamiso are decomposed or converted into odorless compounds during the process of alcoholic fermentation using a yeast, deodorization takes much time, and it is necessary to be extremely careful regarding the management of the alcoholic fermentation process so as to prevent putrefaction and the occurrence of mold. This method also has the problem that, since the deodorized dokudamiso juice contains alcohol in a content substantially the same as that in alcoholic beverages, the juice becomes hard to drink for the aged or infant.

Accordingly, it is an object of the present invention to provide a method of producing a dokudamiso juice by which dokudamiso green juice can be deodorized by a deodorizing method without using alcoholic fermentation to improve the taste and provide the effective components of dokudamiso in a form which allows them to be drunk easily.

It is another object of the present invention to provide a method of effectively producing in a short time a dokudamiso juice which is suitable for drinking and which contains the dokudamiso components having medicinal effects.

SUMMARY OF THE INVENTION

A method of producing a dokudamiso juice in accordance with the present invention comprises the steps of preparing a green juice from fresh dokudamiso, heating or roughly filtering the juice and then oxidizing it.

DETAILED DESCRIPTION OF THE INVENTION

Although any desired method for first preparing dokudamiso green juice can be used, the green juice is generally prepared by grinding dokudamiso, which should be as fresh as possible, for example, crushing it by a hammer crusher, to form a slurry, compressing the slurry formed and then removing the lees. When the cell walls are decomposed by an enzyme such as pectinase or the like which is added in the process of preparing the green juice or to the green juice obtained, the yield of the green juice and the efficiency of the subsequent oxidation are effectively increased.

An appropriate heating apparatus such as a corrugated tube-type heating apparatus is used for heating the thus formed green juice. It is preferable that the heating temperature be 70 to 80° C., and the heating time be about 10 to 30 minutes. A heating temperature of 80° C. or more is unsuitable because it destroys the components having medicinal effects. However, not all the heating process need be effected in a heating apparatus, and the green juice may be heated to the predetermined temperature in a heating apparatus and then transferred to a tank in which the juice is subjected to the above thermal treatment while standing at room temperature.

The heat treatment causes the sterilization of the green juice, and oxidation (owing to the dissolved oxygen) and evaporation of most of the aldehydes, which are the odor components, to produce a green juice having an odor ranging from slightly unpleasant to substantially odorless, in correspondence with the treatment conditions used.

When the green juice obtained is roughly filtered, only solid matter, which is rapidly deposited when the juice is allowed to stand, may be separated. For example, the rough filtration may be carried out by using an appropriate filter, such as a filter press, in which filter cloth is used as a filter medium or by centrifugation which exhibits the same separating effect as caused by the filtration.

Since most microorganisms adhering to the raw dokudamiso material adhere to the lees (sediment) in the green juice, the microorganisms are removed from the green juice by the rough filtration. In addition, since most of the aldehydes, which are the odor components, are filtered off, the unpleasant odor is significantly reduced.

The oxidation is carried out by using oxygen gas, an oxidizing agent, or combination thereof, after the heat treatment or the rough filtration The oxidation by oxygen gas is effected by blowing the oxygen gas into the green juice to generate fine bubbles after the heat treatment or the rough filtration. The oxygen gas may be generated from an oxygen bomb or an oxygen generator, or air from which microorganisms are removed may be used. When an oxidizing agent is used, the oxidizing agent is added to the green juice and mixed therewith in an appropriate reactor or storage vessel, followed by reaction, as occasion demands, under heating. Examples of oxidizing agents that may be used include ammonium persulfate, benzoyl peroxide and the like, which can oxidize the aldehydes to form the corresponding carboxylic acids and which can be used in food. The treatment by combination of oxygen gas and an oxidizing agent is particularly preferable because the purpose of the treatment can be achieved in a very short time. The oxidation treatment causes the complete decomposition of the odor components remaining after the heat treatment or the rough treatment so as to make the juice odorless. The oxidation causes no destruction of the components of dokudamiso having medicinal effects. Although a clear explanation has not been made, it is thought that complicated chemical reactions simultaneously take place between many other components of the green juice to produce a mellow taste in the same way as in ripening of a liquor during preservation after the completion of fermentation. Namely, the dokudamiso juice of the present invention not only has no unpleasant odor but also has pleasant taste and good body. The juice is thus made easier to drink without any hesitation (this change being termed "ripeness" in this specification).

In the present invention, the dokudamiso green juice is deodorized and ripened by the above-mentioned method so that an odorless juice having a good taste and containing the dokudamiso components having medicinal effects can be easily produced in a short time. Since the juice itself obtained is drinkable without any hesitation and has no peculiarities, if flavorings such as sweeteners or souring agents, spices and the like are added to the juice, it can be used as a tasty health drink having the medicinal effects based on quercitrin. The juice can also be used in the production of alcoholic drinks containing components such as quercitrin having medicinal effects if it is fermented by using a yeast and a carbon source such as sugar, honey or the like. The present invention therefore permits the dokudamiso components having medicinal effects to be easily provided at any time in a form which allows easy drinking.

EXAMPLE 1

Fresh dokudamiso was chopped, crushed and squeezed to obtain a green juice containing 4.8 mg/100 g of quercitrin. The thus-obtained green juice was then introduced into a corrugated tube-type heating apparatus used for food in which it was heated at 80° C. for 1 minute. The green juice was then introduced into a tank having no cover in which it was allowed to cool for 4 days.

After heat treatment, although the color of the green juice had changed to ocher, and the unpleasant odor had mostly disappeared, it could be taken only with some reluctance and had a bad taste.

Benzoyl peroxide serving as an oxidizer was added to the juice in an amount of 66 g per kiloliter of the juice, and, at the same time, 15 Kg of oxygen gas was blown into the juice over a time of 8 hours. After the treatment, the juice was a clear amber liquid which gave none of the unpleasant odor peculiar to dokudamiso and was well ripened so as to have a good taste. The juice also contained 4.1 mg/100 g of quercitrin, showing substantially no loss of quercitrin caused by heat treatment and oxidation of the green juice.

EXAMPLE 2

Fresh dokudamiso was chopped, crushed and squeezed to obtain a green juice containing 4.8 mg/100 g of quercitrin. The thus-obtained green juice was roughly filtered by using a filter press.

After filtration, although the unpleasant odor of the green juice mostly disappeared, it could be taken only with some reluctance and had a bad taste.

Benzoyl peroxide serving as an oxidizer was added to the juice in an amount of 66 g per kiloliter of the juice, as well as 15 Kg of oxygen gas being blown into the juice over a time of 8 hours. After the treatment, the juice was a clear amber liquid which gave none of the unpleasant odor peculiar to dokudamiso and was well ripened so as to have a good taste. The juice also contained 4.1 mg/100 g of quercitrin, showing substantially no loss of quercitrin caused by oxidation of the green juice.

What is claimed is:

1. A method of producing an odorless ripe juice of dokudamiso comprising the steps of preparing a green juice from fresh dokudamiso; subjecting said prepared green juice to heat treatment; then oxidizing said heat treated green juice.

2. A method according to claim 1, wherein said heat treatment is carried out at 70° to 80° C. for 10 to 30 minutes.

3. A method of producing an odorless ripe juice of dokudamiso comprising the steps of preparing a green juice from fresh dokudamiso; subjecting said prepared green juice to rough filtration; then oxidizing said filtrated green juice.

* * * * *